United States Patent [19]

Pesa et al.

[11] 4,377,643

[45] Mar. 22, 1983

[54] UPGRADING SYNTHESIS GAS

[75] Inventors: Frederick A. Pesa, Aurora; Anne M. Graham, Northfield, both of Ohio

[73] Assignee: The Standard Oil Company, Cleveland, Ohio

[21] Appl. No.: 332,771

[22] Filed: Dec. 21, 1981

[51] Int. Cl.³ .......................... C07C 1/04; C07C 27/06
[52] U.S. Cl. .................................... 518/713; 518/726; 252/443; 252/460; 252/474
[58] Field of Search ................................ 518/713, 726

[56] References Cited

U.S. PATENT DOCUMENTS

| | | |
|---|---|---|
| 2,535,060 | 12/1950 | Gresham . |
| 2,549,470 | 4/1951 | Howk et al. . |
| 3,941,819 | 3/1976 | Vannice et al. . |
| 4,086,262 | 4/1978 | Chang et al. . |
| 4,096,164 | 6/1978 | Ellgen et al. . |
| 4,101,450 | 7/1978 | Hwang et al. . |
| 4,116,994 | 9/1978 | Vannice et al. . |
| 4,119,656 | 10/1978 | Poutsma et al. . |
| 4,122,110 | 10/1978 | Sugier et al. . |
| 4,136,104 | 1/1979 | Hwang et al. . |
| 4,171,320 | 10/1979 | Vannice et al. . |
| 4,199,522 | 4/1980 | Marchison et al. . |
| 4,210,597 | 7/1980 | Huang . |
| 4,235,798 | 11/1980 | Bartley et al. . |
| 4,246,186 | 1/1981 | Bkasen et al. . |

FOREIGN PATENT DOCUMENTS 18763 11/1980 European Pat. Off. .

OTHER PUBLICATIONS

Galvagm et al., J. of Catalyses, 69, 283–291 (1981).

*Primary Examiner*—Howard T. Mars
*Attorney, Agent, or Firm*—Joseph G. Curatolo; Herbert D. Knudsen; Larry W. Evans

[57] ABSTRACT

Catalysts comprising the mixed oxides of ruthenium, copper, at least one alkali metal and at least one of rhodium, iridium, palladium, and platinum are provided which are useful in the upgrading of synthesis gas, particularly for obtaining alkanes and alcohols.

14 Claims, No Drawings

UPGRADING SYNTHESIS GAS

TECHNICAL FIELD

The present invention is directed to the upgrading of synthesis gas to produce mixtures of hydrocarbons.

More particularly, the present invention is directed to a vapor phase reaction of synthesis gas comprising carbon monoxide and hydrogen in the presence of a catalyst to produce mixtures of hydrocarbon and oxygenated hydrocarbons, wherein alkane and alcohol products predominate.

BACKGROUND OF THE INVENTION

U.S. Pat. Nos. 2,535,060 to Gresham and 2,549,470 to Howk et al. disclose the preparation of straight-chain primary hydroxyalkanes by introducing hydrogen, carbon monoxide and a hydroxylated solvent into a reaction vessel and heating the mixture in the presence of a ruthenium-containing catalyst (particularly ruthenium metal, oxide, carbonyl, or salts of carboxylic acids which give rise to formation of the carbonyl) and in Howk et al., in the presence of an alkaline reagent by maintaining pH in the range of 7.0 to 11.5. Both Gresham and Howk et al. teach that it is essential that the reaction take place in the liquid phase.

U.S. Pat. No. 3,941,819 to Vannice et al. describes the production of ethane, ethylene and dimethyl ether by passing a carbon monoxide and hydrogen mixture over platinum supported on alumina.

U.S. Pat. No. 4,086,262 to Chang et al. describes the production of hydrocarbon mixtures by contacting a mixture of carbon monoxide and hydrogen with a carbon monoxide reduction catalyst and an acidic crystalline alumino silicate (zeolite). Chang et al. teach that prominent types of catalysts include metals for oxides of Zn, Fe, Co, Ni, Ru, Th, Rh, and Os, and that "with the exception of ruthenium, all practical art recognized synthesis catalysts contain chemical and structural promotors".

U.S. Pat. No. 4,096,164 discloses the production of oxygenated 2 carbon atom hydrocarbons by reacting CO and $H_2$ in the presence of catalyst comprising Rh, Mo and W.

U.S. Pat. No. 4,101,450 and U.S. Pat. No. 4,136,104 to Hwang et al. disclose the conversion of synthesis gas to acetic acid and related 2 carbon atom oxygenated derivatives in the presence of a rhodium metal/ruthenium metal catalyst.

U.S. Pat. No. 4,116,994 to Vannice et al. discloses the selective production of olefinic hydrocarbons from carbon monoxide and hydrogen using a catalyst comprising rhodium deposited on titanium containing oxides.

U.S. Pat. No. 4,119,656 describes the production of one to 2 carbon atom oxygenated hydrocarbons by contacting synthesis gas with a catalyst consisting essentially of palladium.

U.S. Pat. No. 4,122,110 to Sugier et al. discloses the manufacture of linear saturated primary alcohols from synthesis gas using a catalyst comprising copper, cobalt, a third metal selected from chromium, iron, vanadium and manganese, at least one alkali metal and optionally zinc.

U.S. Pat. No. 4,171,320 to Vannice discloses the selective production of olefins from carbon monoxide and hydrogen using as a catalyst, ruthenium on a support comprising at least one refractory Group VB metal oxide.

U.S. Pat. No. 4,199,522 to Murchison et al. discloses the preparation of olefins of 2 to 4 carbon atoms from carbon monoxide and hydrogen using catalysts comprising a sulfide, oxide or metal of Mo, W, Re, Ru, Ni, Pd, Rh, Os, Ir or Pt and a hydroxide, oxide or salt of Li, Na, K, Rb, Cs, Mg, Ca, Sr, Ba or Th.

U.S. Pat. No. 4,210,597 to Huang et al. discloses the preparation of oxygenated hydrocarbons by reacting carbon monoxide and hydrogen in the presence of a catalyst containing rhodium, tungsten and an alkali metal.

U.S. Pat. No. 4,246,186 to Bhasin et al. discloses the preparation of two carbon atom oxygenated hydrocarbons from hydrogen and carbon monoxide by reaction with a rhodium metal catalyst, as compared to other single element Group VIII metal and copper catalysts.

European patent application 18,763 by Ball et al. describes the production of oxygenated hydrocarbons having from 1-4 carbon atoms by reacting carbon monoxide and hydrogen in the presence of a catalyst comprising rhodium, chromium and optionally iron, manganese, molybdenum, tungsten or ruthenium. The catalyst may be prepared on a support which has been formerly activated by the addition of metals or non-metals such as alkalis, thorium, manganese, rhodium, iron, chromium, molybdenum, boron, and phosphorus.

SUMMARY OF THE INVENTION

We have found that catalysts comprising the mixed metal oxides of ruthenium, copper, at least one alkali metal, and at least one of rhodium, iridium, palladium or platinum are useful for the upgrading of synthesis gas to hydrocarbons, exhibiting good selectivity to alkanes and oxygenated hydrocarbon products, particularly alcohols.

It is therefore an object of the present invention to provide a process to upgrade synthesis gas to produce hydrocarbons, particularly alkanes and oxygenated hydrocarbons and more particularly alcohols, with high selectivity.

It is a further object of the present invention to provide novel catalyst compositions useful in the upgrading of synthesis gas to produce alkanes and oxygenated hydrocarbons, particularly alcohols.

In general, the process of the present invention includes the upgrading of synthesis gas to obtain selectivity to alkanes and alcohols comprising contacting carbon monoxide and hydrogen in the vapor phase at a reaction temperature of at leaast 250° C. and a reaction pressure of at least 500 psi with a catalyst of the formula

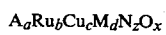

$$A_aRu_bCu_cM_dN_zO_x$$

wherein

A is an alkali metal,

M is Rh, Ir, Pd, Pt or mixtures thereof, and wherein a is about 0.002 to about 0.5, b is about 0.5 to about 3, c is about 0.5 to about 3, d is about 0.05 to about 0.5, z is a level of 0 to about 1 weight % and x is the number of oxygens needed to fulfill the valence requirements of the other elements.

In one embodiment of the invention, the products of the synthesis gas upgrading process are contacted with hydrogen at elevated temperature and pressure in the presence of a hydrogenation catalyst.

The present invention further includes novel catalysts of the composition $$A_aRu_bCu_cM_dN_zO_x$$

wherein
A is an alkali metal,
M is Rh, Ir, Pd, Pt or mixtures thereof, and wherein
a is about 0.002 to about 0.5,
b is about 0.5 to about 3,
c is about 0.5 to about 3,
d is about 0.05 to about 0.5,
z is a level of 0 to about 1 weight % and
x is the number of oxygens needed to fulfill the valence requirements of the other elements.

DETAILED DESCRIPTION OF THE INVENTION

In the process of the present invention, synthesis gas, or a mixture of carbon monoxide and hydrogen, is reacted in the presence of a carbon monoxide hydrogenation catalyst in the vapor phase to form hydrocarbons, and in particular, alkanes and alcohols.

Synthesis gas may be produced by means known in the art and practiced commercially, including providing synthesis gas as product of the partial combustion of coal, natural gas, petroleum bottoms or other carbonaceous materials. One method of derivation is the heating of coke in the presence of air and then steam. The ratio of carbon monoxide to hydrogen in the synthesis gas mixture to be upgraded may vary from about 1:10 to 10:1 and is preferably in the range of about 1:3 to about 3:1. The synthesis gas may contain a very low amount of sulfur compounds, and may also contain small amounts of carbon dioxide, nitrogen and other inerts.

Although synthesis gas is a preferred reactant, any other gas composed primarily of hydrogen and carbon monoxide and having a CO:H2 ratio of about 1:10 to about 10:1 may be employed. Preferably the gaseous reactant is essentially sulfur free.

Process Conditions

The process of the present invention is carried out by contacting the gaseous reactant containing carbon monoxide and hydrogen with the novel catalyst described below in a suitable fluid bed or fixed bed reactor. The reaction can be conducted continuously or in a batch-type operation. The reaction temperature should be maintained between about 250° C. to about 400° C., preferably about 275° C. to about 375° C.

The reaction pressure should normally be maintained between about 500 psi to about 5,000 psi, preferably about 500 psi to about 1500 psi. The reactant gases may be fed to the reactor utilized at a space velocity (liters gaseous reactant fed per liters of catalyst per hour) of about 100 per hour to about 10,000 per hour, preferably about 500 per hour to about 6,000 per hour.

The contact time of the reactants with the catalyst is generally between about 10 seconds to about 200 seconds, and is preferably about 15 seconds to about 140 seconds.

Catalyst

The novel catalyst provided by the present invention is believed to be an oxide complex and comprises the composition described by the empirical formula $$A_aRu_bCu_cM_dN_zO_x$$

wherein
A is an alkali metal,
M is Rh, Ir, Pd, Pt or mixtures thereof, and wherein
a is about 0.002 to about 0.5,
b is about 0.5 to about 3,
c is about 0.5 to about 3,
d is about 0.05 to about 0.5,
z is a level of 0 to about 1 weight % and
x is the number of oxygens needed to fulfill the valence requirements of the other elements.

M is preferably rhodium, iridium or palladium, and A may be selected from Na, Li, K, Rb and Cs, although Na, K and Rb are preferred.

The Ru to Cu ratio is preferably about 1:0.75 to about 1:1.5. The ratio of ruthenium to the promoter metal (M) is generally about 1:0.05 to about 1:0.5 and is preferably about 1:0.1 to about 1:0.5. Alkali metal is required in the catalyst of the present invention. Mixed oxide catalysts of ruthenium and copper which are alkali free produce essentially all methane, at low conversion. The alkali metal may be present in the catalyst at a level of about 0.002 to about 0.5 moles alkali metal per mole of ruthenium. Preferred is a level of about 0.02 to about 0.4 moles alkali metal per mole of ruthenium.

The catalyst of the present invention is a mixed metal oxide. In the process of the present invention, the catalyst is preferably utilized in a partially reduced state. However, the catalyst may not be totally reduced to the metallic state and thus retains its oxide character.

The catalyst may be prepared by conventional means, such as by mixing compounds containing the catalyst components in a liquid solution or slurry, such as a water solution or slurry, and heating, recovering the catalyst precursor from the liquid, drying and calcining. Catalyst component containing compounds may include but are not limited to oxides, hydroxides, inorganic salts such as nitrates, phosphates, halides, carbonates, silicates, aluminates, and salts of organic acids such as acetates, formates, butyrates, propionates, benzylates, and the like. Preferred catalysts of the present invention, containing the alkali metal component are prepared by recovering the catalyst precursor by adding to the aqueous solution of ruthenium, copper and promoter components, an alkali metal hydroxide to cause precipitation of the catalyst precursor, heating in the presence of the alkali metal, and thereafter filtering the precipitate.

The catalyst may be formed in a conventional manner, such as tabletting, pelleting, or supporting the active catalyst material on a carrier. The carrier is preferably inert, and may include silica, alumina, Alundum, clay, alumina-silica, silicon carbide and the like. The active catalytic material may be coated on the carrier by the method described in U.S. Pat. No. 4,077,912 or may be impregnated on the carrier such as by depositing a solution of the catalyst component containing compounds onto a carrier, drying and calcining. The catalyst components may be added to the carrier separately, if desired.

Products

Products of the upgrading of synthesis gas process of the present invention include, among others, methane, ethane, propane, ethylene, methanol, ethanol, propanol, butanol, pentanol, acetic acid, propanoic acid, butyric acid, valeric acid. Small amounts of other alkanes, olefins, and aldehydes are present in the products of the inventive process in some embodiments. These products are useful as chemical feedstocks, or as fuels, such as in gasoline mixtures. Where conversion is maintained at a moderate or low level, these products can be recovered from the reactor effluent, and the remaining synthesis gas recycled to the reaction.

Alkanes, esters and alcohols are most suitable for use as fuels, such as in gasoline mixtures. Therefore, in one embodiment of the invention, the liquid product mixture obtained from the synthesis gas upgrading process (containing in addition to alcohols and esters, the non-fuel components such as olefins, aldehydes and carboxylic acids) is contacted with hydrogen at elevated temperature and pressure in the presence of a hydrogenation catalyst. The resulting hydrogenation products, alkanes, alcohols and esters are suitable for use as fuel components.

The hydrogenation process may be conducted in the vapor phase, at a reaction temperature of about 150° C. to about 450° C. and a reaction pressure of about 250 psig to about 5,000 psig. Any suitable hydrogenation catalyst, such as nickel or copper chromite may be used, but catalysts such as those disclosed in U.S. Ser. No. 264,755, assigned to our common assignee, are preferred. These catalysts may be represented by the formula $$G_e Ru_f D_g E_h O_x$$

wherein

G = Zn, Cd and mixtures thereof;
D = Co, Ni and mixtures thereof;
E = Fe, Cu, Rh, Pd, Os, Ir, Pt and mixtures thereof; and wherein
e = 0 to 1,
f = 0.01 to 3,
g = 0.01 to 3,
h = 0 to 1,
x = the number of oxygens determined by the valence requirements of the other elements.

SPECIFIC EMBODIMENTS

Catalyst Preparation

In the examples below, catalysts were prepared by the following method. An amount of ruthenium chloride and copper chloride required to give 0.03 moles of each metal and an amount of promoter metal component sufficient to provide the desired mole ratio of promoter metal to ruthenium were dissolved in 250 milliliters of water with stirring for 30 minutes. Aqueous sodium hydroxide (50% by weight) was added dropwise, with stirring, until the pH reached and remained at 8.3 to 8.5 (approximately 7 to 15 milliliters). The resulting slurry was heated near boiling for 30 minutes with constant stirring, then cooled. The pH was adjusted if necessary to 7.5. The mixture was filtered, and washed, and reslurried with subsequent filtering and washing steps until the molar ratio of sodium to ruthenium present was approximately about 0.02 to about 0.2:1. The solid mixed oxide was dried at 125° C. for about 16 hours, was calcined for three hours at about 350° C. (in air) and was ground to pass 140 mesh (0.105 millimeters).

The catalysts were coated upon alumina-silica supports in the following manner. 25 grams of Norton SA 5223 Alundum, 10/30 mesh (0.595 millimeters–2.00 millimeters) were placed in a vessel. 1.25 grams distilled water was sprayed onto the Alundum which was rolled for approximately 10 minutes and the procedure was repeated. The metal oxide catalysts, in an amount calculated to give a total of 0.015 moles of active metal, were added in two equal portions with 15 minutes rolling after each. The coated catalyst was dried for about 16 hours at 125° C. and calcined three hours at 350° C. Catalysts prepared in this manner contain approximately 5 weight percent active metals, 0.01% to 0.1% by weight sodium and have surface areas of about 2 m²/g, with pore volumes of from about 0.06 to about 0.09 cc/g.

The catalysts were partially reduced in the following manner. A stainless steel tube reactor was packed with catalyst, and hydrogen gas was introduced into the reactor at 150–200 cc/min. at atmospheric pressure. The electric block furnace placed around the reactor was increased in 50° increments stepwise until 500° C. was reached. The final temperature was maintained for two hours, at which time the reactor was allowed to cool with hydrogen flow being continued.

In one embodiment of the invention, catalysts are nitrided after reduction by contacting the catalyst with ammonia for several hours at atmospheric pressure and a temperature of about 400° C., with subsequent cooling under ammonia. The nitrided catalysts contain up to 1 weight percent nitrogen, as is preferred. Between 0.5 to 1 weight percent nitrogen is most preferred.

Reaction Procedure

Following catalyst reduction, nitriding and subsequent cooling to room temperature, the 20 cc reactor utilized was charged to the desired pressure with hydrogen. The split block electric furnace surrounding the reactor was activated and set for run temperature. The system was allowed to equilibrate for at least 15 minutes at run temperature before carbon monoxide flow was started and both gases were adjusted to the desired flow rates. After about one to one and one-half hours of reaction, the off-gas (effluent) was sampled and analyzed and the condensible product diverted from a pre-run receiver to a product collection receiver. A recovery run proceeded for one to three hours during which time the off-gas was analyzed by gas chromatography and its volume measured. The liquid product also was weighed and analyzed.

In addition to gas chromatography analysis for the gas phase, hydrocarbons having greater than three carbon atoms were determined by flame ionization detection. Liquid phase hydrocarbons and oxygenated hydrocarbons were analyzed by gas chromatography. The results reported in the Table below were calculated as follows.

CO Conversion =

$$\frac{\text{Moles of CO input} - \text{moles CO effluent} \times 100}{\text{Moles of CO input}}$$

$$\text{Weight \%} = \frac{\text{Weight product identified} \times 100}{\text{Total product weight}}$$

Carbon dioxide and water were not considered in the calculations.

The catalysts identified in the examples below were prepared according to the catalyst preparation method set forth above. The catalysts were reduced, nitrided and tested for synthesis gas upgrading by the reaction procedure set forth above. Reaction and test results are set forth in the Table below.

EXAMPLES 1-4

Catalysts of the formula 5% $Na_aRuCuRh_{0.5}N_zO_x$/95% Alundum were prepared and tested according to the procedures first set forth above. Rhodium chloride was utilized as the promoter element containing compound. Products of the synthesis gas upgrading reaction utilizing these catalysts were predominantly alkanes and alcohols.

EXAMPLE 5

A catalyst of the formula 5% $Na_aRuCuRh_{0.1}N_zO_x$/95% Alundum was prepared and tested according to the procedure of Examples 1-4 except that a lower level of rhodium was utilized in the catalyst preparation. The catalyst was selective to alkanes and alcohol production, with olefin and carboxylic acid production increasing.

EXAMPLES 6-7

Catalysts of the formula 5% $Na_aRuCuIr_{0.5}N_zO_x$/95% Alundum were prepared and tested according to the procedure of Examples 1-4 except that iridium chloride was substituted for rhodium chloride. Products of the synthesis gas upgrading reaction utilizing these catalysts were predominantly alkanes and alcohols.

EXAMPLES 8-9

Catalysts of the formula 5% $Na_aRuCuPd_{0.5}N_zO_x$/95% Alundum were prepared and tested according to the procedure of Examples 1-4 except that palladium acetate was substituted for rhodium chloride in the preparation. Products of the synthesis gas upgrading reaction utilizing these catalysts were predominantly alkanes and alcohols.

Comparative Example 10

A catalyst of the formula 5% $Na_aRuCuN_zO_x$/95% Alundum was prepared and tested according to the procedure of Examples 1-4, except that no promoter metal (M) was added in the catalyst preparation. Products of the synthesis gas upgrading reaction utilizing this catalyst were predominantly carboxylic acids.

As an example of the product mixture produced by the inventive process, the products obtained by testing the catalyst of Example 1 are as follows.

| Product | Wt. (grams) |
| --- | --- |
| Methane | 0.0500 |
| Ethylene | 0.0123 |
| Methanol | 0.1075 |
| Ethanol | 0.0136 |
| Propanol | 0.0027 |
| Butanol | 0.0017 |
| Pentanol | 0.0022 |
| Acetic Acid | 0.0043 |
| Propanoic Acid | 0.0055 |
| Butyric Acid | 0.0051 |
| Valeric Acid | 0.0096 |

Thus it should be apparent to those skilled in the art that the subject invention accomplishes the objects set forth above. It is to be understood that the subject invention is not to be limited by the examples set forth herein. These have been provided merely to demonstrate operability and the selection of catalyst component containing compounds, catalyst formulations, synthesis gas component ratios and reaction conditions can be determined from the total specification disclosure provided without departing from the spirit of the invention herein disclosed and described, the scope of the invention including equivalent embodiments, modifications and variations that fall within the scope of the attached claims.

TABLE

SYNTHESIS GAS UPGRADING USING 5% $M_dNa_aCuRuN_zO_x$/95% ALUNDUM CATALYSTS

| Example No. | $M_d$ Promoter | $CO:H_2$ Ratio | Temp. °C. | Pressure (psig) | Space Velocity $Hr^{-1}$ | % CO Conv. | Weight % Useful Products | | | |
| --- | --- | --- | --- | --- | --- | --- | --- | --- | --- | --- |
| | | | | | | | Alkanes | Olefins | Carboxylic Acids | Alcohols |
| 1 | $Rh_{0.5}$ | 7:3 | 360 | 1300 | 2000 | 6.2 | 23.3 | 5.7 | 11.4 | 59.5 |
| 2 | $Rh_{0.5}$ | 3:7 | 360 | 1300 | 3300 | 2.6 | 86.8 | — | 2.0 | 11.2 |
| 3 | $Rh_{0.5}$ | 3:7 | 350 | 1300 | 2000 | 5.5 | 33.6 | — | 10.3 | 56.1 |
| 4 | $Rh_{0.5}$ | 1:1 | 360 | 1300 | 2000 | 5.6 | 36.8 | 6.2 | 7.8 | 49.1 |
| 5 | $Rh_{0.1}$ | 3:7 | 350 | 1300 | 3300 | 20.5 | 35.2 | 21.3 | 29.1 | 10.6 j |
| 6 | $Ir_{0.5}$ | 3:7 | 360 | 1300 | 2000 | 11.6 | 85.4 | — | 1.8 | 12.8 |
| 7 | $Ir_{0.5}$ | 7:3 | 360 | 1300 | 2000 | 3.1 | 61.5 | 4.4 | 8.0 | 26.0 |
| 8 | $Pd_{0.5}$ | 3:7 | 350 | 1300 | 3300 | 14.0 | 84.6 | — | 0.7 | 14.6 |
| 9 | $Pd_{0.5}$ | 3:7 | 320 | 1000 | 5500 | 3.6 | 79.5 | — | 0.3 | 20.2 |
| C10 | — | 3:7 | 320 | 1000 | 5500 | 4.0 | 14.3 | 8.3 | 63.0 | 5.2 k | a = 0.002–0.02
j = less than 4% aldehydes and esters (combined) also present.
k = 5.5% aldehydes, 3.8% esters
z = 0.5–1 weight % active catalyst

We claim:
1. A process for the upgrading of synthesis gas to obtain selectivity to alkanes and alcohols comprising contacting carbon monoxide and hydrogen in the vapor phase at a reaction temperature of at least 250° C. and a reaction pressure of at least 500 psi with a catalyst of the formula

$$A_aRu_bCu_cM_dN_zO_x$$

wherein
A is an alkali metal, wherein
M is Rh, Ir, Pd, Pt or mixtures thereof and wherein
a is about 0.02 to about 0.5,
b is about 0.5 to about 3,
c is about 0.5 to about 3,
d is about 0.05 to about 0.5,
z is a level of 0 to about 1 weight % and
x is the number of oxygens needed to fulfill the valence requirements of the other elements.
2. A process as in claim 1 wherein A is selected from sodium, potassium and rubidium.

3. A process as in claim 1 wherein a is about 0.02 to about 0.4.

4. A process as in claim 1 wherein b and c are each about 1.

5. A process as in claim 4 wherein d is about 0.1 to about 0.5.

6. A process as in claim 1 wherein said catalyst is partially reduced.

7. A process as in claim 1, 5 or 6 wherein said catalyst is supported on an inert carrier.

8. A process as in claim 7 wherein said carrier is selected from alumina, silica, alumina-silica, Alundum, clay, and silicon carbide.

9. A process as in claim 1 wherein the ratio of carbon monoxide to hydrogen is 10:1 to 1:10.

10. A process as in claim 1 wherein the ratio of carbon monoxide to hydrogen is 3:1 to 1:3.

11. A process as in claim 1 wherein the reaction temperature is about 275° C. to about 375° C.

12. A process as in claim 1 wherein the reaction pressure is about 500 psi to about 5000 psi.

13. A process as in claim 1 further including the steps of contacting the resulting products of the upgrading of synthesis gas with hydrogen at elevated temperature and pressure in the presence of a hydrogenation catalyst.

14. A process as in claim 13 wherein said hydrogenation catalyst is represented by the formula $$G_e Ru_f D_g E_h O_x$$

wherein
G = Zn, Cd and mixtures thereof;
D = Co, Ni and mixtures thereof;
E = Fe, Cu, Rh, Pd, Os, Ir, Pt and mixtures thereof; and
wherein
e = 0 to 1,
f = 0.01 to 3,
g = 0.01 to 3,
h = 0 to 1,
x = the number of oxygens determined by the valence requirements of the other elements.

* * * * *